United States Patent [19]

Connor et al.

[11] Patent Number: 4,767,776
[45] Date of Patent: Aug. 30, 1988

[54] N-1H-TETRAZOL-5-YL-2-NAPHTHALENE CARBOXAMIDES AND THEIR USE AS ANTIALLERGY AND ANTIINFLAMMATORY AGENTS

[75] Inventors: David T. Connor; Paul C. Unangst, both of Ann Arbor, Mich.; Robert J. Weikert, Santa Clara, Calif.

[73] Assignee: Warner-Lambert Company, Morris Plains, N.J.

[21] Appl. No.: 16,811

[22] Filed: Feb. 20, 1987

[51] Int. Cl.[4] .................. C07D 257/04; A61K 31/41
[52] U.S. Cl. ..................................... 514/381; 548/251
[58] Field of Search .................. 548/251; 514/381

[56] References Cited

U.S. PATENT DOCUMENTS

| 3,824,249 | 7/1974 | Regnier et al. | 548/251 |
| 3,887,574 | 6/1975 | Ellis et al. | 548/251 |
| 4,145,350 | 3/1979 | Hodson et al. | 548/251 |
| 4,146,631 | 3/1979 | Ford et al. | 548/251 |
| 4,147,694 | 4/1979 | Erickson | 546/169 |
| 4,432,986 | 2/1984 | Erickson | 548/252 |
| 4,474,792 | 10/1984 | Erickson | 548/251 |

Primary Examiner—Richard L. Raymond
Assistant Examiner—D. B. Springer
Attorney, Agent, or Firm—Joan Thierstein

[57] ABSTRACT

Novel naphthalene derivatives having antiallergy and antiinflammatory activity.

14 Claims, No Drawings

N-1H-TETRAZOL-5-YL-2-NAPHTHALENE CARBOXAMIDES AND THEIR USE AS ANTIALLERGY AND ANTIINFLAMMATORY AGENTS

BACKGROUND OF THE INVENTION

Various N-1H-tetrazol-5-yl carboxamides are disclosed having use as antiallergy agents. Particularly, U.S. Pat. No. 4,432,986 issued Feb. 21, 1984 discloses polycyclic carboxamides having the formula

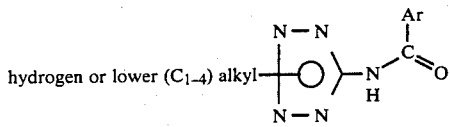

where Ar includes the polycycle:

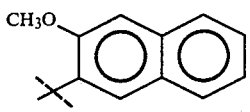

Contrary to the disclosure of U.S. Pat. No. 4,432,986 the present invention is for a compound having an alkoxy or alkylthio at the 1-position of 2-naphthalenecarboxamide. That is, the pattern of substituents of the compounds of the present invention is different from the disclosure of U.S. Pat. No. 4,432,986.

In fact, U.S. Pat. No. 4,432,986 teaches a positioning of particular substituents for especially potent anti-allergic compounds. Thus, the disclosure teaches away from the positioning of the present invention compounds. Further, it is now found the compounds of the present invention are particularly potent as inhibitors of histamine release from human basophils which is contrary to that expected for the compounds as disclosed in U.S. Pat. No. 4,432,986 by an ordinarily skilled artisan. In fact, the 3-methoxy naphthalene polycycle described above from U.S. Pat. No. 4,432,986 does not inhibit histamine release from human basophils.

Of lesser interest are teachings to the compounds of U.S. Pat. Nos. 3,887,574 which are amides of aminotetrazole and acid-substituted chromones, xanthones and anthraquinones; 4,145,350 which are selected tricyclic compounds having tetrazolyl groups among the substituents; 4,147,694 which are optionally substituted 8-(1H-tetrazol-5-ylcarbamoyl)quinolines; and 4,232,024 which are also compounds including a COX moiety where X may be tetrazolyl-5-amino. Such compounds are antiallergenic but do not add any teaching to the level of skill in the art pertinent to the present invention.

Similarly, applications (assigned to the assignee of the present invention) which disclose a tetrazolyl-5-amino carbonyl moiety are U.S. Ser. No. 790,664 and U.S. Ser. No. 788,111. However, compounds of such applications are derivatives of benzofuran and benzothiophene and indole ring systems respectively. Among the utilities for the compounds of these applications is antiallergy.

SUMMARY OF THE INVENTION

The present invention is a novel compound of the formula (I)

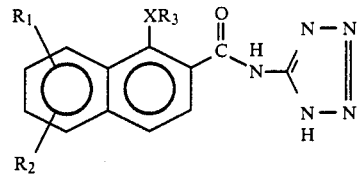

wherein X is oxygen or sulfur; $R_3$ is alkyl of from one to twelve carbons and $R_1$ and $R_2$ are independently hydrogen, lower alkyl, lower alkoxy, mercapto, halogen, trifluoromethyl, lower alkylthio, lower alkylsulfinyl, lower alkylsulfonyl, hydroxy, nitro, amino, mono-lower alkyl or di-lower alkyl amino, or $R_1$ and $R_2$ taken together are methylene dioxy, with the proviso that mixed oxidation states of sulfur are not present; or pharmaceutically acceptable salts thereof.

The present invention also relates to pharmaceutical composition containing the compounds of formula I and to methods of treating allergy in mammals, particularly humans, in need thereof.

DETAILED DESCRIPTION

Alkyl of from one to twelve carbons means methyl, ethyl, propyl, butyl, pentyl, hexyl, heptyl, octyl, nonyl, decyl, undecyl, dodecyl and isomers thereof.

Lower alkyl is a hydrocarbon chain of one to six carbons including methyl, ethyl, propyl, butyl, pentyl, or hexyl and isomers thereof.

Lower alkoxy is of from one to six carbons including methoxy, ethoxy, propoxy, butoxy, pentoxy or hexoxy and isomers thereof.

Halogen is fluoro, chloro, bromo, or iodo.

The tetrazole ring in the compounds of the invention exists in tautomeric form such that the hydrogen is on either the $N^1$ or $N^2$ atoms of the ring, i.e.,

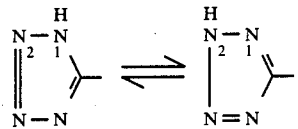

However, for convenience, hydrogen is depicted herein simply as appearing on the $N^1$ atom.

The novel compounds of formula I are named as derivatives of naphthalene by virtue of fused benzo rings. The fused rings are numbered clockwise starting with the carbon having the $XR_3$ attached as follows:

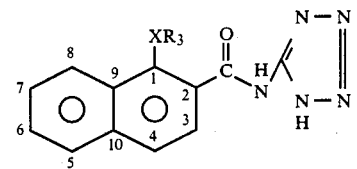

Certain compounds within the scope of formula I are preferred, since they have a more advantageous pharmacological effect.

The $R_1$ and $R_2$ groups are preferably attached at the 5- and 6- or 7- and 8-positions.

More preferably the $R^1$ and $R^2$ groups are attached to the 6- or 7-position and are independently either hydrogen or methoxy respectively and wherein $R_3$ is isopropyl.

The most preferred compound is 7-methoxy-1-(1-methylethoxy)-N-1H-tetrazol-5-yl-2-naphthalenecarboxamide.

In general, the procedure for preparing the novel compounds of the present invention is as shown in the following Scheme I.

thoic acid of formula 5 having $R_1$ and $R_2$ as defined above by the use of: (1) potassium bicarbonate using procedures analogous to the Kolbe-Schmitt reaction; see A. S. Lindsey and H. Jeskey, *Chem. Rev.*, 57, 583 (1957) or, (2) magnesium methyl carbonate (known as the Stiles reagent) using procedures analogous to those of L. A. Cate, *Synthesis*, 385 (1983). Naphthoic acid of the formula 5 is esterified to yield naphthoic enol ester

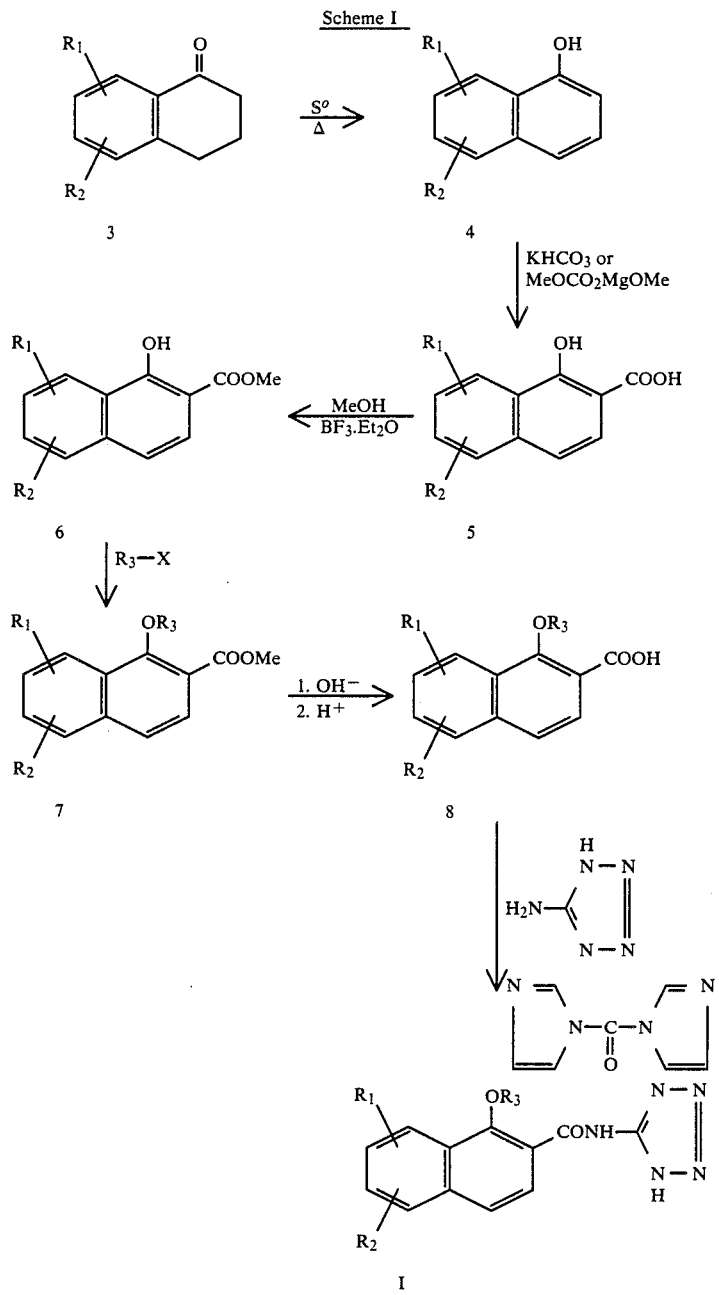

A tetralone compound of formula 3 wherein $R_1$ and $R_2$ are as defined above (commercially available, or prepared by the Haworth synthesis; for example, see L. F. Fieser and A. M. Seligman, *J. Amer. Chem. Soc.*, 170 (1938)) is heated with sulfur in order to aromatize the tetralone and yield naphthol of formula 4 having $R_1$ and $R_2$ as defined above. For example, see A. J. Shand and R. H. Thomson, *Tetrahedron*, 19, 1919 (1963). The naphthol of the formula 4 is carboxylated to yield naphof formula 6 having $R_1$ and $R_2$ as defined above, and the enolic OH group of the formula 6 is then aklylated to yield alkoxy ester of formula 7 wherein $R_1$, $R_2$, and $R_3$ are as defined above. Reagents for alkylation include alkyl halides, alkyl sulfonates, and isoureas. See L. J. Mathias, *Synthesis*, 561 (1979). Alkoxy esters of the formula 7 are frequently oils and the crude product is saponified to yield alkoxy acids of formula 8 wherein $R_1$, $R_2$, and $R_3$ are as defined above. The acid of the formula 8 is converted to the carbamoyltetrazole of the formula I as defined above by coupling with 5-aminotetrazole. Coupling reagents can include 1,1'-carbonyldiimidazole, DCC(1,3-dicyclohexylcarbodiimide), or other peptide-coupling reagents.

Salts of the compound of the formula I can be prepared by reacting with inorganic or organic bases such as is described below.

An alternate synthetic route to intermediates of the formula 6 is shown in Scheme II.

scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include

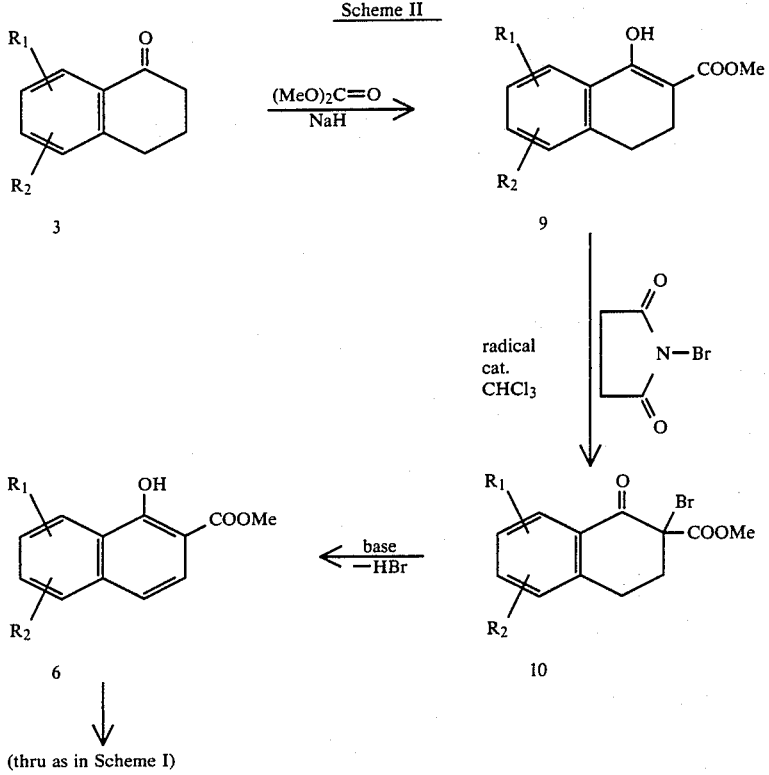

Tetralone of the formula 3 as defined for Scheme 1 is converted to the enolic keto-ester of formula 9 wherein $R_1$ and $R_2$ are as defined above, by carboxylation with dimethyl carbonate and sodium hydride. This procedure is analogous to that of D. W. Johnson and L. N. Mander, *Aust. J. Chem.*, 27, 1277 (1974). For an additional analogous route to a compound of the formula 9, see W. E. Bachmann and D. G. Thomas, *J. Amer. Chem. Soc.*, 64, 94 (1942). The ester of the formula 9 is brominated with N-bromosuccinimide in the presence of a free radical initiator. Catalysts that can be used for this purpose include benzoyl peroxide, $\alpha,\alpha$-azoisobutyronitrile ("AIBN"), and others. The bromoester intermediate of formula 10 wherein $R_1$ and $R_2$ are as defined above is treated with a base to effect dehydrohalogenation and yield the naphthalene enol ester of the formula 6. Among the bases that can be employed are pyridine, N,N-diethylaniline, 1,8-diazabicyclo[5.4.-0]undec-7-ene ("DBU"), and others.

The starting materials required for the processes described in this invention are either commercially available or can be synthesized by methods known in the art.

The compounds of formula I are useful both in the free acid form, in the form of base salts, and in the form of acid addition salts. The three forms are within the the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1), 1–19 (1977).)

The acid addition salts of said basic compounds are prepared either by dissolving the free base of compound I in aqueous or aqueous alcohol solution or other suitable solvents containing the appropriate acid or base, and isolating the salt by evaporating the solution, or by reacting the free base of compound I with an acid, as well as reacting compound I having an acid group thereon with a base such that the reactions are in an organic solvent, in which case the salt separates directly or can be obtained by concentration of the solution.

The base salts of compounds of formula I described above are prepared by reacting the appropriate base with a stoichometric equivalent of the acid compounds of formula I to obtain pharmacologically acceptable base salts thereof.

The acid solution salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may also exist in hydrated or solvated forms.

The products of the reactions described herein are isolated by conventional means such as extraction, distillation, chromatography and the like.

The antiallergic activity not within that expected of the compounds having the formula I of the present invention is shown by an assay determining inhibition of the release of histamine from human basophils (HHB). A description of the protocol for the HHB assay is found hereinafter.

Thus, pharmaceutical compositions are prepared from the compounds of formula I and salts thereof described as the present invention in unit dosage form comprising the compound either alone or in admixture with a pharmaceutically acceptable carrier appropriately selected from those known.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies. They may also be introduced parenterally (e.g., subcutaneously, intravenously, or intramuscularly), using forms known to the pharmaceutical art. They are also introduced directly to an affected area, (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound I is employed in treatment. The ordinarily skilled physician or veterinarian will readily determine and prescribe the effective amount of the antiallergic or antiinflammatory agent to prevent or arrest the progress of the condition. The dosage regimen is selected in accordance with a variety of factors including the type, age, weight, sex, and medical condition of the mammal, the severity of symptoms of the disease being treated, the route of administration and particular compound of formula I employed. An ordinarily skilled physician or veterinarian will readily determine and prescribe the effective amount of the compound I to prevent or arrest the progress of the condition. In so proceeding, the physician or veterinarian could employ relatively low dosages at first, subsequently increasing the dose until a maximum response is obtained. For convenience, the total daily dosage may be divided and administered in portions during the day if desired. In so proceeding the physician or veterinarian could employ relatively low dosages at first, subsequently increasing the dose until a maximum response is obtained.

Initial dosages of the compounds of the invention having formula I are ordinarily in the area of 10 mg up to 2 g per day orally, preferably 10 mg to 500 mg per dose orally, given from one to four times daily or as needed. When other forms of administration are employed equivalent doses are administered.

It is understood that the compositions and methods of treatment of the present invention as described above also include the free acid, the pharmacologically acceptable base salts and acid addition salts of the compounds of formula I.

The following examples further illustrate the invention, but are not meant to be limiting thereto.

EXAMPLE 1

6-Methoxy-1-naphthalenol

A mixture of 50.0 g (0.28 mole) of 6-methoxy-1-tetralone and 9.2 g (0.29 mole) of elemental sulfur was stirred and heated at 250°–260° for three hours (until the evolution of hydrogen sulfide gas had ceased). The mixture was cooled and then subjected to bulb-to-bulb distillation. The distillate was dissolved in 300 ml of dichloromethane, and the solution was extracted with 1.0N potassium hydroxide solution (3×150 ml). The base extracts were combined, cooled in ice, and acidified with 10% hydrochloric acid to precipitate the crude naphthol product as a gum. Trituration of the gum with tert-butyl methyl ether yielded 16.8 g (34% yield) of the analytically pure naphthol, mp 84°–86° (a mp of 83°–84° is given by M. P. Sibi, J. W. Dankwardt, and V. Snieckus, *J. Org. Chem.*, 51, 271 (1986)).

Calcd. for $C_{11}H_{10}O_2$: C, 75.84; H, 5.79. Found C, 75.66; H, 5.69.

Also prepared by a procedure analogous to the above procedure from the appropriate tetralone were:

EXAMPLE 2

5-Methoxy-1-naphthalenol

Mp 136°–138° (a mp of 136°–138° is given by M. P. Sibi, et al., cited above).

Calcd. for $C_{11}H_{10}O_2$: C, 75.84; H, 5.79; Found C, 75.88; H, 5.84,

EXAMPLE 3

7-Methoxy-1-naphthalenol

Mp 105°–107° (a mp of 103°–105° is given by A. J. Shand and R. H. Thomson, *Tetrahedron*, 19, 1919 (1963)).

Calcd. for $C_{11}H_{10}O_2$: C, 75.84; H, 5.79; Found C, 75.49; H, 5.85, and

EXAMPLE 4

7-(1-Methylethoxy)-1-naphthalenol

Mp 127°–129°.

Calcd. for $C_{13}H_{14}O_2$: C, 77.20; H, 6.98; Found C, 77.48; H, 6.87.

EXAMPLE 5

3,4-Dihydro-7-hydroxy-1(2H)-naphthalene

A flask containing 164 g (1.42 mole) of pyridine hydrochloride in a nitrogen atmosphere was stirred and heated to 190°. After 30 minutes, 50.0 g (0.28 mole) of 7-methoxy-1-tetralone was added in one portion, and heating at 190° was continued for two hours. The mixture was cooled and poured over 2.0 kg of ice/water. The precipitated solid was filtered and washed with water to yield 37.7 g (97% yield) of the analytically pure phenol product, mp 154°-156° (a mp of 159° is given by J. V. Braun, Ann., 451, 1 (1927)).

Calcd. for $C_{10}H_{10}O_2$: C, 74.06; H, 6.21; Found C, 74.06; H, 6.22.

EXAMPLE 6

3,4-Dihydro-7-(1-methylethoxy)-1(2H)-naphthalenone

A suspension of 24.3 g (0.22 mole) of potassium tert-butoxide in 240 ml of dimethyl sulfoxide under a nitrogen atmosphere was stirred and cooled in a cold water bath while a solution of 29.2 g (0.18 mole) of 3,4-dihydro-7-hydroxy-1(2H)-naphthalenone in 400 ml of dimethyl sulfoxide was added dropwise over 45 minutes. The mixture was stirred at room temperature for an additional 45 minutes, and then 23.7 ml (31.0 g; 0.25 mole) of 2-bromopropane was added in one portion. After stirring for an additional 30 hours, the mixture was added to 2.0 kg of ice/water and extracted with dichloromethane (4×300 ml). The combined organic layers were back-washed with water (2×150 ml), dried (anhydrous magnesium sulfate), and evaporated (vacuum) to an oil residue. Flash chromatographic purification (silica gel, dichloromethane elution) of the residue yielded 24.0 g (65% yield) of the analytically pure ether product as an oil, suitable for conversion to the naphthol described in Example 4.

Calcd. for $C_{13}H_{16}O_2$: C, 76.44; H, 7.90; Found C, 76.44; H, 7.86.

EXAMPLE 7

1-Hydroxy-6-methoxy-2-naphthalenecarboxylic acid

A mixture of 14.0 g (0.080 mole) of 6-methoxy-1-naphthalenol and 100 ml (0.25 mole) of a 2.5M solution of magnesium methyl carbonate in N,N-dimethylformamide were sealed in a 300 cc pressure reactor and pressurized to 550 psi with nitrogen gas. The reactor was heated to 180° for six hours without agitation, cooled, and then the reaction mixture was added to 1.75 kg of ice/water. The mixture was acidified with 6.0N aqueous hydrochloric acid. The precipitated crude product was filtered, stirred in 350 ml of fresh water, and re-filtered. The solid was dissolved with warming in 600 ml of 5% aqueous sodium bicarbonate solution, and the solution was decolorized with activated charcoal. The filtrate from the charcoal treatment was cooled, washed with ethyl acetate (2×400 ml), cooled in ice, and again acidified with 6.0N aqueous hydrochloric acid. The precipitated product was filtered and washed with water to yield 14.0 g (80% yield) of the analytically pure hydroxy acid, mp 188° dec.

Calcd. for $C_{12}H_{10}O_4$: C, 66.05; H, 4.62; Found: C, 66.36; H, 4.74.

Also prepared by a procedure analogous to the above procedure of Example 7 using the appropriate naphthol were:

EXAMPLE 8

1-Hydroxy-5-methoxy-2-naphthalenecarboxylic acid

Mp 197°-dec. (a mp of 212.5°-213° is given by P. Hill, W. F. Short, and H. Stromberg, J. Chem. Soc., 937 (1937)).

Calcd. for $C_{12}H_{10}O_4 \cdot 0.25H_2O$: C, 64.71; H, 4.75; Found C, 64.38; H, 4.75,

EXAMPLE 9

1-Hydroxy-7-methoxy-2-naphthalenecarboxylic acid

Mp 196°-dec.

Calcd. for $C_{12}H_{10}O_4 \cdot 0.25H_2O$: C, 64.71; H, 4.75; Found C, 65.06; H, 4.62, and

EXAMPLE 10

1-Hydroxy-7-(1-methylethoxy)-2-naphthalenecarboxylic acid

Mp 189° dec.

Calcd. for $C_{14}H_{14}O_4$: C, 68.28; H, 5.73; Found C, 68.29; H, 5.76.

EXAMPLE 11

1-Hydroxy-7-methoxy-2-naphthalenecarboxylic acid, methyl ester

A suspension of 6.2 g (0.028 mole) of 1-hydroxy-7-methoxy-2-naphthalenecarboxylic acid in 75 ml of methanol under a nitrogen atmosphere was treated over 15 minutes with 15.0 ml (17.3 g; 0.12 mole) of boron trifluoride etherate. The mixture was stirred at reflux for 45 hours, cooled, and added slowly to 500 ml of ice cold 5% aqueous sodium bicarbonate solution. The precipitated product was filtered, and washed with water to yield 6.0 g (92% yield) of the ester, mp 80°-83°, suitable for further synthetic use. A sample purified by chromatography (silica gel, dichloromethane elution) was analytically pure, mp 79°-81° (a mp of 81°-82° is given by M. E. Alonso, A. W. Chitty, S. Pekerar, and M. de L. Borgo, J. Chem. Soc. Chem. Comm., 1542 (1984).

Calcd. for $C_{13}H_{12}O_4$: C, 67.23; H, 5.21; Found C, 67.33; H, 5.18.

Also prepared by a procedure analogous to the above procedure of Example 11 using the appropriate carboxylic acid were:

EXAMPLE 12

1-Hydroxy-2-naphthalenecarboxylic acid, methyl ester

Mp 74°-76° (a mp of 76°-77° is given by N. J. P. Broom and P. G. Sammes, J. Chem. Soc. Perk. I, 465 (1981)).

Calcd. for $C_{12}H_{10}O_3$: C, 71.28; H, 4.98; Found C, 71.06; H, 5.03,

EXAMPLE 13

1-Hydroxy-5-methoxy-2-naphthalenecarboxylic acid, methyl ester

Mp 114°-116° (a mp of 118°-119° is given by P. Hill, et al., previously cited).

Calcd. for $C_{13}H_{12}O_4$: C, 67.23; H, 5.21; Found C, 67.37; H, 5.14,

EXAMPLE 14

1-Hydroxy-6-methoxy-2-naphthalenecarboxylic acid, methyl ester

Mp 108°–110°.

Calcd. for $C_{13}H_{12}O_4$: C, 67.23; H, 5.21; Found C, 67.27; H, 5.15, and

EXAMPLE 15

1-Hydroxy-7-(1-methylethoxy)-2-naphthalenecarboxylic acid, methyl ester

Mp 77°–79°.

Calcd. for $C_{15}H_{16}O_4$: C, 69.22; H, 6.20; Found C, 69.17; H, 6.45.

EXAMPLE 16

6-Methoxy-1-(1-methylethoxy)-2-naphthalenecarboxylic acid

A suspension of 5.2 g (0.046 mole) of potassium tert-butoxide in 45 ml of dimethyl sulfoxide under a nitrogen atmosphere was treated over 20 minutes with a solution of 7.5 g (0.032 mole) of 1-hydroxy-6-methoxy-2-naphthalenecarboxylic acid, methyl ester in 80 ml of dimethyl sulfoxide. The mixture was stirred for 45 minutes, then treated in one portion with 4.6 ml (6.0 g; 0.049 mole) of 2-bromopropane. The mixture was stirred at room temperature for 72 hours, then added to 750 g of ice/water. The alkoxy-ester intermediate was separated by extracting with dichloromethane (3×150 ml). The combined organic extracts were washed with water (1×200 ml), 0.5N aqueous potassium hydroxide solution (2×200 ml), and water again. The organic layer was dried (anhydrous magnesium sulfate) and evaporated (vacuum) to yield 7.9 g (90% yield) of the crude intermediate 6-methoxy-1-(1-methylethoxy)-2-naphthalenecarboxylic acid, methyl ester as a yellow oil.

The total crude residue described above was dissolved in 50 ml of methanol and treated with a solution of 4.2 g (0.075 mole) of potassium hydroxide in 50 ml of water. The mixture was stirred at reflux for two hours, cooled, and added to 500 g of ice/water. Acidification with 6.0N hydrochloric acid yielded the crude carboxylic acid product as a gum. The gum was extracted with dichloromethane (3×75 ml), and the combined extracts were back-washed with water (1×150 ml), dried (anhydrous magnesium sulfate), and evaporated. Trituration of the residue with ether/hexane yielded 5.7 g (68% yield) of the analytically pure carboxylic acid product, mp 138°–141°.

Calcd. for $C_{15}H_{16}O_4$: C, 69.21; H, 6.20; Found C, 69.54; H, 6.16.

Also prepared by a procedure analogous to the above procedure of Example 16 using the appropriate hydroxy ester were:

EXAMPLE 17

1-(1-Methylethoxy)-2-naphthalenecarboxylic acid

Mp 109°–111°.

Calcd. for $C_{14}H_{14}O_3$: C, 73.02; H, 6.13; Found C, 73.13; H, 6.38,

EXAMPLE 18

5-Methoxy-1-(1-methylethoxy)-2-naphthalenecarboxylic acid

Mp 129°–131°.

Calcd. for $C_{15}H_{16}O_4$: C, 69.21; H, 6.20; Found C, 68.91; H, 5.96,

EXAMPLE 19

7-Methoxy-1-(1-methylethoxy)-2-naphthalenecarboxylic acid

Mp 106°–109°.

Calcd. for $C_{15}H_{16}O_4$: C, 69.21; H, 6.20; Found C, 68.98; H, 6.32, and

EXAMPLE 20

1,7-bis(1-Methylethoxy)-2-naphthalenecarboxylic acid

Mp 90°–92°.

Calcd. for $C_{17}H_{20}O_4$: C, 70.81; H, 6.99; Found C, 70.72; H, 7.11.

EXAMPLE 21

1,7-Dimethoxy-2-naphthalenecarboxylic acid

A mixture of 3.7 g (0.016 mole) of 1-hydroxy-7-methoxy-2-naphthalenecarboxylic acid, methyl ester and 2.9 g (0.021 mole) of anhydrous potassium carbonate in 20 ml of N,N-dimethylformamide under a nitrogen atmosphere was treated with 3.0 ml (6.8 g; 0.048 mole) of iodomethane. The mixture was stirred at room temperature for 24 hours, and then added to 150 g of ice/water. The crude intermediate ester was separated by extracting with dichloromethane (3×50 ml). The combined organic layers were washed with water (2×50 ml), dried (anhydrous magnesium sulfate) and evaporated (vacuum).

The total crude residue obtained above was saponified as described in Example 16. The analytically pure carboxylic acid product was 2.7 g (73% yield), mp 130°–132°.

Calcd. for $C_{13}H_{12}O_4$: C, 67.23; H, 5.21; Found C, 67.32; H, 5.23.

EXAMPLE 22

6-Methoxy-1-(1-methylethoxy)-N-1H-tetrazol-5-yl-2-naphthalenecarboxamide

A mixture of 4.5 g (0.017 mole) of 6-methoxy-1-(1-methylethoxy)-2-naphthalenecarboxylic acid and 3.2 g (0.020 mole) of 1,1'-carbonyldiimidazole in 40 ml of acetonitrile under a nitrogen atmosphere was stirred at reflux for one hour. The mixture was cooled, treated with 1.7 g (0.020 mole) of anhydrous 5-aminotetrazole and 5.6 ml (4.1 g; 0.040 mole) of triethylamine, and again stirred at reflux for five hours. The reaction mixture was cooled, added to 500 g of ice/water, and acidified with glacial acetic acid. The precipitated solid was filtered and washed with water to yield 5.4 g (97% yield) of the analytically pure carbamoyltetrazole product, mp 265°-dec.

Calcd. for $C_{16}H_{17}N_5O_3$: C, 58.72; H, 5.24; N, 21.40; Found C, 58.89; H, 5.30; N, 21.00.

Also prepared by a procedure analogous to the above procedure of Example 22 using the appropriate carboxylic acid were:

EXAMPLE 23

1-(1-Methylethoxy)-N-1H-tetrazol-5-yl-2-naphthalenecarboxamide

Mp 267° dec.

Calcd. for $C_{15}H_{15}N_5O_2$: C, 60.59; H, 5.09; N, 23.56; Found C, 60.79; H, 5.33; N, 23.55,

EXAMPLE 24

1,7-Dimethoxy-N-1H-tetrazol-5-yl-2-napthalenecarboxamide

Mp 242° dec.
Calcd. for $C_{14}H_{13}N_5O_3$: C, 56.18; H, 4.38; N, 23.40; Found C, 56.22; H, 4.25; N, 23.13,

EXAMPLE 25

5-Methoxy-1-(1-methylethoxy)-N-1H-tetrazol-5-yl-2-naphthalenecarboxamide

Mp 278° dec.
Calcd. for $C_{16}H_{17}N_5O_3$: C, 58.72; H, 5.24; N, 21.40; Found C, 58.43; H, 5.18; N, 21.54,

EXAMPLE 26

7-Methoxy-1-(1-methylethoxy)-N-1H-tetrazol-5-yl-2-naphthalenecarboxamide

Mp 252° dec.
Calcd. for $C_{16}H_{17}N_5O_3$: C, 58.72; H, 5.24; N, 21.40; Found C, 58.32; H, 5.04; N, 21.49, and

EXAMPLE 27

1,7-bis(1-Methylethoxy)-N-1H-tetrazol-5-yl-2-naphthalenecarboxamide

Mp 235° dec.
Calcd. for $C_{18}H_{21}N_5O_3$: C, 60.83; H, 5.96; N, 19.71; Found C, 60.44; H, 5.82; N, 19.78.

EXAMPLE 28

6-Methoxy-1-(1-methylethoxy)-N-1H-tetrazol-5-yl-2-naphthalenecarboxamide, sodium salt A suspension of 3.27 g (0.010 mole) of 6-methoxy-1-(1-methylethoxy)-N-1H-tetrazol-5-yl-2-naphthalenecarboxamide in 30 ml of methanol was treated with 5.0 ml of 2.00N aqueous sodium hydroxide solution. The mixture was digested on the steam bath for several minutes and filtered hot. The cooled filtrate was evaporated (vacuum) to one-half of its original volume. The solution was cooled in an ice bath, and the precipitated solid was filtered and washed several times with cold methanol to yield 3.0 g (87% yield) of the analytically pure sodium salt, mp 190° dec.

Calcd. for $C_{16}H_{16}N_5O_3Na$: C, 55.01; H, 4.62; N, 20.05; Found C, 55.03; H, 4.81; N, 20.09.

EXAMPLE 29

7-Methoxy-1-(1-methylethoxy)-N-1H-tetrazol-5-yl-2-naphthalenecarboxamide, sodium salt A suspension of 5.5 g (0.017 mole) of 7-methoxy-1-(1-methylethoxy)-N-1H-tetrazol-5-yl-2-naphthalenecarboxamide in 200 ml of methanol was treated with 8.5 ml of 2.00N aqueous sodium hydroxide solution. The mixture was digested on the steam bath for ten minutes and filtered hot. The cooled filtrate was evaporated (vacuum) to dryness, and the residue was re-dissolved several times in 2-propanol and re-evaporated. Trituration of the final residue with acetonitrile yielded 5.1 g (86% yield) of the analytically pure sodium salt containing 0.25 equivalent of water of hydration, mp 193°–197°.

Calcd. for $C_{16}H_{16}N_5O_3Na.0.25H_2O$: C, 54.31; H, 4.70; N, 19.80; Found C, 54.06; H, 4.53; N, 19.66.

EXAMPLE 30

1,2,3,4-Tetrahydro-6-methoxy-1-oxo-2-naphthalenecarboxylic acid, methyl ester

A suspension of 24.0 g (0.60 mole) of sodium hydride (60% dispersion in mineral oil) and 49.5 ml (52.9 g; 0.59 mole) of dimethyl carbonate (freshly distilled from sodium hydride) in 240 ml of tetrahydrofuran under a nitrogen atmosphere was stirred and heated to reflux. Reflux was maintained while a solution of 29.7 g (0.17 mole) of 6-methoxy-1-tetralone in 105 ml of tetrahydrofuran was added dropwise over two hours. After addition was complete, the mixture was stirred at reflux for an additional 90 minutes, cooled in ice, and treated dropwise with 36 ml of glacial acetic acid, followed by 450 ml of ice water. The two-phase reaction mixture was extracted with ethyl acetate (4×250 ml), and the combined organic layers were washed with water (1×600 ml), 5% aqueous sodium bicarbonate solution (3×600 ml), and water again. The ethyl acetate extract was dried (anhydrous sodium sulfate and evaporated (vacuum). The residue was pulverized and stirred in 500 ml of hexane. Filtration yielded 37.9 g (96% yield) of the ester product, mp 79°–81°, suitable for further synthesis. A sample purified by bulb-to-bulb distillation followed by recrystallization from hexane/ethyl acetate was analytically pure, mp 82°–84° (a mp of 88°–89° is given by J. Jacques and A. Horeau, *Bull. Soc. Chem. France*, 512 (1950)).

Calcd. for $C_{13}H_{14}O_4$: C, 66.65; H, 6.02; Found C, 66.69; H, 6.00.

EXAMPLE 31

1,2,3,4-Tetrahydro-2-bromo-6-methoxy-1-oxo-2-naphthalenecarboxylic acid, methyl ester A solution of 5.2 g (0.022 mole) of 1,2,3,4-tetrahydro-6-methoxy-1-oxo-2-naphthalenecarboxylic acid, methyl ester in 40 ml of chloroform under a nitrogen atmosphere was treated, in portions, with 4.4 g (0.025 mole) of N-bromosuccinimide, followed by 0.025 g (0.00015 mole) of α,α-azobisisobutyronitrile. The mixture was stirred at reflux for one hour, cooled in ice, and diluted with 30 ml of hexane. The precipitated succinimide by-product was filtered and discarded. Evaporation (vacuum) of the filtrate and recrystallization of the residue from ether/petroleum ether yielded 5.1 g (73% yield) of the analytically pure bromo ester, mp 99°–101°.

Calcd. for $C_{13}H_{13}BrO_4$: C, 49.86; H, 4.18; Br, 25.52; Found C, 49.79; H, 4.16; Br, 25.40.

EXAMPLE 32

1-Hydroxy-6-methoxy-2-naphthalenecarboxylic acid, methyl ester (alternate procedure)

A solution of 10.2 g (0.033 mole) of 1,2,3,4-tetrahydro-2-bromo-6-methoxy-1-oxo-2-naphthalenecarboxylic acid, methyl ester in 100 ml of tetrahydrofuran under a nitrogen atmosphere was treated over 15 minutes with a solution of 10.0 ml (10.2 g; 0.067 mole) of 1,8-diazabicyclo[5.4.0]undec-7-ene in 20 ml of tetrahydrofuran. The mixture was stirred at room temperature for 16 hours, then added to 450 g of ice/water. Acidification with 6.0N hydrochloric acid precipitated the crude naphthalene ester product. The solid was filtered, washed with water, and recrystallized from aqueous methanol to yield 5.1 g (67% yield) of the final product, mp 109°–111°. This material was identical with that prepared by the procedure described in Example 11.

The usefulness of the compounds of the present invention as inhibitors of histamine release is demonstrated by the following tests, particularly the assay for histamine release from human basophils or HHB. The HHB test is essentially as generally accepted among the ordinarily skilled artisans to show activity having unique usefulness to treat the diseases or conditions as set out in the present invention. Additionally, the fragmented lung analphylaxis test, or FLAT, is generally accepted among the ordinarily skilled artisan to show activity having usefulness to treat the diseases or conditions set out herein. A description of each procedure follows.

HISTAMINE RELEASE FROM HUMAN BASOPHILS (hereinafter HHB)

The HHB assay quantitates active histamine release and its inhibition by drugs, from gasophils of human blood. Thus, the assay provides evaluation of the compounds of formula I for treating the conditions or diseases as is the present invention. As described herein the assay includes modifications of the method described by R. P. Siraganian in "An Automated Continuous-Flow System for the Extraction and Fluorometric Analysis of Histamine", *Anal. Biochem.*, 57, 383–394 (1974).

Methods

Preparation of Leukocytes

Seventy ml of blood are drawn from allergic donors (chosen on the basis of adequate histamine induced by a challenge), using standard venipuncture methods, into 10 ml Vacutainers with 0.08 ml/tube 15% EDTA in water as anticoagulant. The blood samples are placed briefly on a rotary mixer. All glassware contacting the blood is siliconized. The blood is aliquoted into three plastic 50 ml centrifuge tubes and the volume is noted. Hespan (hydroxy ethyl starch), 0.5 ml per 1.0 ml of blood, is added. The tubes are inverted several times to mix and are left undisturbed at room temperature until a sharp separation is observed between the settled red cells and the leukocyte and platelet-rich plasma. This usually occurs within 35–45 minutes.

The plasma fraction is pipetted off and placed into two clean plastic 50 ml centrifuge tubes. The tubes are centrifuged for 12 minutes at 4° in a Sorval RC-3 centrifuge with an HL-8 rotor at 1050 RPM (100 g). The platelets remain in the plasma and are discarded. The pelleted leukocytes are shaken gently to disrupt the cell button and washed twice as described:

Wash 1. Five ml of HA buffer with 0.005M EDTA is added to the dispersed cells in each tube and gently vortexed. 25 ml of buffer is then added and gently vortexed. The samples are again centrifuged as described earlier. The supernatant is poured off, and the cell button in each tube is gently dispersed.

Wash 2. Five ml of HA buffer with EDTA is added to each tube to resuspend the cells. Leukocytes are then pooled into one tube and the volume is brought up to 40 ml with HA buffer with EDTA and gently vortexed. The pooled sample is centrifuged at 1050 RPM for 12 minutes. The supernatant fluid is discarded and the cell button is dispersed. Sixteen ml of HACM buffer is added to the washed cells and gently vortexed. A sample is prepared for Hematology, where a total white blood cell and platelet count is done using a Coulter Counter.

Aliquots (0.1 ml) of cells are added to assay tubes containing 0.4 ml of either 6% perchloric acid (for total histamine content), vehicle control (for spontaneous release), or drug. The tubes are incubated at room temperature for 8 minutes, and then placed in a 37° water bath for two more minutes. Buffer or challenge agents (at 37°) are added to the tube and they are incubated for an additional 45 minutes at 37°. The tubes are then spun at 2000 RPM (1200 g) for three minutes to pellet the cells and the supernatants are poured into assay cups.

Drug Preparation

A 300 $\mu$M stock solution of each test compound is prepared as follows: an appropriate amount of compound (molecular weight/33.33) is weighed out into a 100 ml volumetric flask and 0.5 ml DMSO is added. If the compound does not dissolve readily, it is warmed gently on a hot plate and approximately 30 ml of distilled water is added. If the compound is in solution, distilled water is used to bring it up to 100 ml total volume. If the drug is not in solution, 0.2 ml 1N NaOH (or HCl) is added, and then distilled water is added to yield 100 ml total solution. Five ml of the stock solution is diluted (1:2) with 5 ml of two times concentrated HACM (Hepes Albumin Calcium Magnesium) buffer to yield the stock working concentration of 150 $\mu$M. When added to the cells and stimulus, a final test concentration of 100 $\mu$M drug results (400 $\mu$l drug, 100 $\mu$l cells and 100 $\mu$l challenge agent or vehicle). Further dilutions are made with HACM buffer for 33, 10, 3.3, 1.0 $\mu$M, etc.

Challenge Agent Preparation

Short ragweed and house dust extracts (Greer Laboratories, Inc.) are supplied as aqueous extracts in stock concentrations of 40,000 and 10,000 protein nitrogen units per milliliter (PNU/ml), respectively. Aqueous solutions of anti-IgE antisera (rabbit-raised antibody) are purchased from Dako via Accurate Chemicals. The tripeptide f-met-leu-phe (fmlp) from Vega Biochemicals is used. The aqueous solutions of ragweed, house dust, and anti-IgE are diluted 1:2 with two times concentrated HACM and then further diluted with HACM to yield final stock concentrations of 6000 PNU/ml for ragweed and house dust, and a 1:50 dilution for the anti-IgE antisera. For fmlp, 28.5 mg of the tripeptide is dissolved in 1 ml of DMSO or 1 ml glacial acetic acid, then 49 ml distilled water and 50 ml of two times HACM are added to yield a final stock of 600 $\mu$M in HACM. The pH is adjusted to 7.4. Further dilutions for working solutions are made in HACM buffer. All stock and working solutions are stored at 4°. Working solutions comprise 1/6 of the final volume in the cell reaction, therefore, working solutions of challenge agents are made up six times the required final concentration (i.e., 600 $\mu$M f-met-leu-phe yields 100 $\mu$M final concentration in the cellular reaction).

Protocol Design

Samples are run in triplicate, using either 1.5 ml polypropylene-capped reaction tubes, or 5.0 ml plastic uncapped tubes. Test compounds and challenge agents are prepared in HACM buffer, as described above. Fixed volume pipettes are used.

Test compound or vehicle control is added to three reaction tubes at 1.5× the final desired concentration (i.e., 400 $\mu$l of test compound per 600 $\mu$l total reaction volume). One hundred $\mu$l of cells is added to each tube and the mixture is incubated for eight minutes at room temperature, and two minutes at 37° before antigen or other stimulus challenge. One hundred μl of the challenge agent at 6× the final concentration is then added, and the final mixture is incubated at 37° for 45 minutes in a shaking water bath. This ensures that the cell preparation is constantly in suspension. The reaction is stopped by centrifugation at 2000 RPM for three minutes at 4°. The supernate ($\approx 500$ μl) is poured into 2.0 ml autoanalyzer beakers and assayed for histamine by the fluorometric method.

In each experiment, cells from one donor are challenged with one or more of the challenge agents, according to the designed protocol and the previously determined sensitivity of the donor to particular challenge agents. Short ragweed and house dust concentrations are expressed in PNU/ml, fmlp challenges are in micromolar concentration (μM), and anti-IgE antisera and C5a challenges are in dilutions, e.g., 1E-5 (1:100,000), 3E-5 (1:30,000), and 1E-4 (1:10,000).

Calculation and Interpretation of Results

The total concentration in the "total" (acid-treated) samples must be 15 ng/ml to be acceptable. Spontaneous release of histamine from the cells should not exceed 15% of the total histamine, and is frequently <5%. The maximum percentage histamine released varies with the donor. The net amount released by the challenge agent must exceed 25% of the total cellular histamine to confidently assess inhibition by test compounds. Spontaneous histamine release is subtracted from both "totals" and challenged cells to calculate net percent release. Percent inhibition is calculated using the following formula:

$$1 - \left[ \frac{\text{Mean net \% release treated samples}}{\text{Mean net \% release for challenged control}} \right] \times 100 = \% \text{ inhibition}$$

Using the HHB assay the compounds of formula I are generally shown by the examples tested to inhibit the release of histamine from human basophils challenged with antigen and, thus, to have activity different from that expected by an ordinarily skilled artisan.

The results are shown in the table as follows:

HHB TEST TABLE

| Example No. | % Inhibition of Histamine Release with Anti-IgE Stimulus (tested at [33 μM]) |
| --- | --- |
| 23 | 16 |
| 24 | 57 |
| 25 | 11 |
| 22 | 71 |
| 26 | 91 |
| 27 | 0 at highest dose tested |

Accordingly, the present invention also includes a pharmaceutical composition for treating one of the above diseases or conditions comprising an antidisease or anticondition effective amount of a compound of the formula I as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compound of formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents. It can also be encapsulating material. In powders, the carrier is a finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these in packaged form.

The quantity of active compound in a unit dose of preparation may be varied or adjusted from 10 mg to 2,000 mg preferably to 10 to 500 mg according to the particular application and the potency of the active ingredient. The compositions can, if desired, also contain other compatible therapeutic agents.

What is claimed is:

1. A compound of the formula (I)

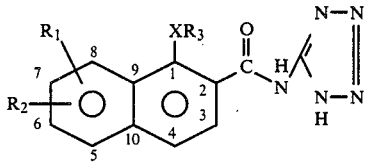

wherein
X is oxygen or sulfur;
$R_3$ is alkyl of from one to twelve carbons; and
$R_1$ and $R_2$ are independently hydrogen, lower alkyl, lower alkoxy, mercapto, halogen, trifluoromethyl, lower alkylthio, lower alkylsulfinyl, lower alkylsulfonyl, hydroxy, nitro, amino, mono loweralkyl or di loweralkyl amino, or taken together are methylenedioxy, with the proviso that S cannot have mixed oxidation states; and pharmaceutically acceptable salts thereof.

2. A compound of claim 1 wherein $R_3$ is isopropyl.
3. A compound of claim 1 wherein X is oxygen.
4. A compound of claim 1 wherein $R_1$ and $R_2$ are at the 5- and 6- or 7- and 8-position.
5. A compound of claim 3 wherein the compound is 6-methoxy-1-(isopropoxy)-N-1H-tetrazol-5-yl-2-naphthalenecarboxamide.
6. The sodium salt of claim 5.
7. A compound of claim 3 wherein the compound is 1-(1-isopropoxy)-N-1H-tetrazol-5-yl-2-naphthalenecarboxamide.
8. A compound of claim 3 wherein the compound is 1,7-dimethoxy-N-1N-tetrazol-5-yl-2-naphthalenecarboxamide.
9. A compound of claim 3 wherein the compound is 5-methoxy-1-(isopropoxy)-N-1N-tetrazol-5-yl-2-naphthalenecarboxamide.
10. A compound of claim 3 wherein the compound is 7-methoxy-1-(isopropoxy)-N-1H-tetrazol-5-yl-2-naphthalenecarboxamide.
11. The sodium salt of claim 10.
12. A compound of claim 3 wherein the compound is 1,7-bis(isopropoxy)-N-1H-tetrazol-5-yl-2-naphthalenecarboxamide.
13. A pharmaceutical composition for treating diseases or conditions having an advantageous effect from inhibition of histamine release from basophils which comprises an inhibitory release from basophil effective amount of a compound of claim 1 and a pharmaceutically acceptable carrier.
14. A method of treating mammals to inhibit histamine release from basophils which comprises administering to mammals which have an advantageous effect therefrom a compound of claim 1 in unit dosage form.

* * * * *

UNITED STATES PATENT AND TRADEMARK OFFICE
CERTIFICATE OF CORRECTION

PATENT NO. : 4,767,776

DATED : August 30, 1988

INVENTOR(S) : David T. Connor, et al.

It is certified that error appears in the above—identified patent and that said Letters Patent is hereby corrected as shown below:

In column 20 line 16 change "(1-isopropoxy)" to --(isopropoxy)--.

Signed and Sealed this

Twenty-fourth Day of January, 1989

Attest:

DONALD J. QUIGG

*Attesting Officer*  *Commissioner of Patents and Trademarks*